United States Patent [19]

Jansson et al.

[11] Patent Number: 4,877,746

[45] Date of Patent: Oct. 31, 1989

[54] METHODS OF CARRYING OUT ASSAYS FOR LIPOPROTEINS AND APOLIPOPROTEINS

[75] Inventors: Gunnel B. Jansson, Alunda; Erling S. Holmlund, Vattholma, both of Sweden

[73] Assignee: Pharmacia AB, Upsala, Sweden

[21] Appl. No.: 49,997

[22] PCT Filed: Sep. 12, 1986

[86] PCT No.: PCT/SE86/00405

§ 371 Date: Apr. 21, 1987

§ 102(e) Date: Apr. 21, 1987

[87] PCT Pub. No.: WO87/02137

PCT Pub. Date: Apr. 9, 1987

[30] Foreign Application Priority Data

Sep. 27, 1985 [SE] Sweden .................................. 8504466

[51] Int. Cl.⁴ .............................................. G01N 33/53
[52] U.S. Cl. .................................... 436/518; 436/536; 436/543; 436/804; 436/815; 436/825; 435/7
[58] Field of Search ............... 435/7; 436/13, 71, 516, 436/518, 536, 543, 175, 804, 815, 825, 826

[56] References Cited

PUBLICATIONS

Milthorp et al. Chemical Abstracts 105: 4747h (1986).
Watt et al. PNAS(U.S.A.) 80, 124–128, (1983).
Bury-I Clinical Chem. 32(2), 265–270 (1986).
Bury-II Clinical Chem. 31(2), 247–251 (1985).
Mao et al. Biochimica et Biophysica Acta 620, 447–453 (1980).

Primary Examiner—Robert Benson
Attorney, Agent, or Firm—Fred Philpitt

[57] ABSTRACT

Method for carrying out immunochemical assays for lipoproteins and/or apolipoproteins, wherein prior to the reaction of the sample with the appropriate anti(apolipoprotein) or anti(lipoprotein) antibody the pH of the sample is maintained at a non-denaturing value in a pretreatment step for exposing antigenic determinants, said non-denaturing value lying above pH 9.0 or below pH 3.0. After the pre-treatment step the pH is adjusted for immune reaction, so that then the immunochemical assay can be carried out in a manner known per se.

4 Claims, No Drawings

METHODS OF CARRYING OUT ASSAYS FOR LIPOPROTEINS AND APOLIPOPROTEINS

The present invention relates to a novel method of treating samples to be subjected to qualitative and/or quantitative immunochemical assays for lipoproteins or, especially, apolipoproteins. Present immunochemical methods require an anti(apolipoprotein or anti(lipoprotein) antibody to react with its corresponding antigen.

Lipoproteins consist of aggregates in which triglycerides, phospholipids, cholesterol and its esters, free fatty acids and proteins bind to one another non-covalently. Proteins present in lipoproteins are often referred to as "apolipoproteins", their individual names comprising the prefix "apo" followed by the type name of the protein. Thus for instance there are proteins apoAI, apoAII, apoB, apoCI, apoCII, apoCIII, apoD, apo(a), and apoE. Some of these apolipoproteins may have isoforms. Also so-called polymorphism may occur.

Lipoproteins as they exist in their form of whole aggregates are often classified according to size and density. There are thus chylomicrons, VLDL, LDL, Lp(a) (where Lp means lipoprotein) and HDL. These in turn may be divided into various subgroups. The majority of apolipoproteins have been shown to exist in more than one size fraction, the only exception being apo(a) which up to now has been detected only in Lp(a) where it occurs together with apoB.

Many apolipoproteins have been shown to possess a receptor-binding and/or enzyme-controlling function. They are believed to be very important in lipid metabolism.

The serum and plasma levels of various lipo- and apolipoproteins have been correlated with genetic and acquired diseases. Moreover it has been possible to correlate these levels with some potential disease contraction risks. In particular, increased levels of apo(a) and Lp(a) are considered to indicate a cardiovascular risk.

Lipoproteins in different fractions of blood have been separated from one another by means of inter alia ultracentrifugation, chromatography, precipitation with polyanions, and electrophoresis. The separated lipoproteins have then been quantified and characterized with the aid of i.a. the apolipoproteins present therein. This has been carried out by means of various immunochemical as well as other methods.

Among the assay methods for detection of apolipoproteins may be mentioned: radial immunodiffusion, electroimmuno-, radioimmuno- and enzyme-immunological methods, isoelectric focusing, nephelometry, turbdimetry, polyacrylamide electrophoresis and densitometry. It goes without saying that other detection methods too may be employed, as for instance fluorescence and chemiluminescence methods.

Lipoproteins and apolipoproteins, their structure and quantification, and the clinical implications of their serum and plasma levels have been dealt with in a major number of handbooks and review articles (see for example Newman H. A. I. et al.: Immunological Assay of Lipoproteins as an Indicator of Genetic and Acquired Disease; and Gibson J. C. et al.: Laboratory Management/1983/, March, p. 19-27 and April, p. 27-37).

It turned out to be difficult to standardize immunochemical assays for lipo- and apolipoproteins. What would happen quite often was that results obtained from different laboratories and different testing occasions were found to differ inter se. It has been shown that the treatment of the test sample was an important factor. Differences between results have been found to originate from inter alia the phenomenon that non-reproducible changes tend to arise due to storage of a sample. To avoid these problems, various experiments have been made for achieving delipidation of samples with the aid of lipid-dissolving solvents, different types of detergents and enzymatic hydrolysis (e.g. by lipase), the underlying idea being that one should thus obtain improved exposures of the antigenic determinants present in the lipoproteins. However none of the delipidating methods have been found to be really successful.

During the priority year the Swedish Patent Office has performed an International Type Search stressing that this is a correct description of the Prior Art situation. They have cited:

1. Mills G. L. et al.: A Guidebook to lipoprotein Technique (in Laboratory Techniques in Biochemistry and Molecular Biology (Elsevier) 14(1984) p. 421-48 and 463-71), EP-A-No. 130,537 and U.S. Pat. No. 4,311,788 disclose pretreatment methods of the clearing of turbid (lipemic) serum and plasma samples. In order to adapt the samples to an immunoassay protocol (esp. nephelometry) certain tensides, and/or lipid-degrading (hydrolytic) enzymes are used in a pretreatment step.

2. Albers J. J. et al.: International Symposium on Artherosclerosis 5th (Berlin) 1979, p. 811-15 (Published 1980) recognize the importance of demasking antigenic determinants on apolipoproteins (particularly apoB) by an hydrolytic treatment of the appropriate sample. The publication stresses that the demasking problem has not been circumvented yet.

4. Kupke I. R.: Clin Chimica Acta 95(1979) p. 123-7 disclose a method for the determination of a non-proteinic constituent (cholesterol) in lipoproteins.

5. Nestruck A. C. et al.: Biochim Biphys Acta 617(1980) p. 110-2; Heuck C-Chr et al.: J Biol Chem 258(1983) p. 8317-22; and Kohwi Y. et al.: Biochem 23(1984) p. 5945-50 relate to the characterization of apolipoproteins without discussing anything about their quantification.

A first object of this invention is to provide a method for stabilizing samples which are to be subjected to immunochemical assays for apolipoproteins. A second object is to improve the reproducibility of the protein assays. A third object is to improve the reliability of diagnoses of diseases correlated with anomalous levels of some apolipo- or lipo-protein. A fourth object is to provide a method of exposing antigenic determinants of apolipoproteins, especially apo(a).

The invention provides improved methods for studying and immunochemically assaying for isoforms and polymorphism or the aforesaid type of proteins.

These objects are attained according to the invention in that prior to the reaction of the sample with the desired anti(apolipoprotein) antibody or anti(lipoprotein) antibody the pH of the sample is maintained, in a pretreatment step, at a non-denaturing value above about pH 9.0 or below about pH 3.0, preferably outside the pH range 3.0-9.0. The sample is maintained at this pH for a time and at a temperature sufficient for optimally exposing the lipoprotein antigenic determinants to an immune reaction. As a last step of the pretreatment according to the invention, the pH is adjusted to the value required for the immune reaction so that then the immunochemical assay can be performed in a manner known per se.

The term "non-denaturing value" means that the pH value is to be one at which apolipo- or lipoprotein antigenic determinants of crucial importance for the test are not destroyed by for instance hydrolysis or irreversible changes.

The sample may be a whole blood sample or various fractions thereof, e.g. plasma or serum fractions. Or it may consist of one of the lipoprotein fractions naturally occurring in blood (as for example chylomicrons, VLDL, LDL, Lp(a) or HDL) which has been separated out in a known per se manner.

During the pretreatment step the pH is preferably adjusted to a value within the range of 0–3, as e.g. 0–2.5, or to a value within the range of 9.0–14.0; this latter range is the one preferably chosen, and within this range pH values above about 10 are preferred, as e.g. above 11 but below 13. The pH adjustment may be carried out by means of non-buffering acids, for instance hydrochloric acid, or with non-buffering alkaline solutions, for instance sodium hydroxide. It is of course preferred to employ diluted solutions, which will facilitate an appropriate control of the additions to be made. It is also feasible to adjust the pH with the aid of buffer systems having a high buffering capacity within the above-mentioned ranges. Suitable buffer systems are acid-base pairs having pKas within the said ranges, for example $H_3PO_4/H_2PO_4^-$ and $Cl_3COOH/Cl_3COO^-$ for pH 0–3, and $HPO_4^{2-}/PO_4^{3-}$ for pH 9–14. For pH values higher than 9.0 the concentration of hydroxide ion and/or added buffering components is higher than $10^{-5}$ M, for example higher than $10^{-3}$ M, and suitably less than 2 M, e.g. less than 0.5 M. For pH values of less than 3 the concentration of $H_3O^+$ and/or added buffering components is higher than $10^{-3}$ M, as e.g. higher than $10^{-2.5}$ M, and is suitably less than 2 M.

If desired various lipid-dissolving enzymes may be added which are active at the pH at which the pretreatment step is carried out. The buffering capacity during the pretreatment step should be such as to permit easy adjustment to the pH value required for the subsequent immunochemical assay. During the pretreatment acidic substances are released; this indicates that the sample is being partially hydrolyzed. The buffering capacity should be high enough to neutralize released substances.

The efficiency of the pretreatment step may be studies in relation to the immunochemical assay to be employed subsequently. Thus for instance optimum temperature, time and pH conditions can be determined by means of determining in separate experiments how each of these variables affects the actual test procedure to be carried out. In the working examples, this has been done with a so-called sandwich procedure. Too high temperatures and concentrations and too long pretreatment times may turn out to be conducive to denaturing effects in the apolipoproteins; this means a decreased uptake in the sandwich method.

The pretreatment step of this invention is preferably carried out at a temperature within the range of 0°–50° C., with 10°–40° C. being most preferred. The pretreatment step may be one of a series of many pretreatment steps.

Temperature and concentrations of acid and base should be chosen such that their values will not cause denaturation at the pH chosen.

The duration of the pretreatment is determined by practical considerations. The temperature and pH are chosen such that the pretreatment step can be carried out within a time in the range of from 5 minutes to 20 hours, preferably 5 min.–5 hrs.

Performing the immunochemical assay in a manner known per se means that it is possible to use any desired immunochemical method of sufficient sensitivity and specificity. For lipoproteins and apolipoproteins, a great number of such methods are known; see for instance the prior art mentioned above. The pretreatment step of this invention is potentially useful for all of these methods. In particular may be mentioned those employing at least one immunochemical reactant which possesses an analytically detectable group, e.g. an enzymatically active (enzyme, coenzyme, cofactor, substrate etc.), radioactive, chemiluminogenic, fluorogenic, particulate (virus, latex, gold) group.

In these assays it is sometimes possible to utilize biospecific affinities other than and equivalent to the affinity between an antigen (hapten) and its corresponding antibody. Examples of materials having such other affinities are protein A—IgG; carbohydrate—lectin; Clq-immune complex; RF factor—immune complex; biotin—avidin etc.

With the results currently obtained the invention is applicable very advantageously to immunochemical assays for lipoprotein(a) or apo(a).

Particularly great advantages are obtained with immunochemical methods in which a labeled immunochemical reactant is utilized for quantifying specific apolipoproteins without a preceding separation of these proteins inter se—as e.g. quantifying inserum, plasma and whole blood.

The invention will now be illustrated by means of a number of non-limitative examples. It is clearly demonstrated, thus, that the invention is superior to earlier methods for delipidation of samples which are to be subjected to immunochemical assays for lipoproteins and apolipoproteins.

REAGENTS:

Phosphate buffer I (pH 7.0, 0.05 M) containing Tween®20 (0.1%), bovine serum albumin (1%), EDTA (0.01 M), and bacteriostatic (0.15%).

Antiapo lipoprotein antisera. Goal antiapo(a), sheep antiapo(a), rabbit antiapoAI and rabbit antiapoB antisera were prepared in a known manner by immunization with Lp(a), apoAI and LDL.

Monoclonal antibodies against apo(a) and apoB (mouse antiapo(a) and mouse antiapoB) were prepared by hybridizing mouse myeloma cells with spleen cells from mice immunized with pure Lp(a) and LDL, respectively. Hybridization and subsequent culturing and cloning of the hybrids were carried out according to: Research Monographs in Immunology Vol. 3 General editor I. L. Turk, Elsevier/North Holland, Biomedical Press, New York 1981.

$^{125}$I-labeled monoclonal antiapo(a) antibody (=mouse antiapo(a) $^{125}$I) was prepared by labelling mouse antiapo(a) with $^{125}$I according to the chloramine-T method (Hunter & Greenwood, Nature 194/1962/p.495).

Mouse monoclonals directed towards apoAI were purchased from Medical Diagnostics Inc (Cambridge, UK). They were labeled by the chloramine-T method.

Decanting suspension (Pharmacia AB, Uppsala, Sweden) contains horse-antisheep-IgG or sheep-antirabbit-IgG antibodies covalently bound to agarose particles. The reagent with antisheep antibodies can be used because horse-antisheep-IgG antibodies will strongly cross react with goat IgG.

SDS=sodium dodecyl sulfate.

Renex®30=detergent from Atlas Chemical Industries, England

Triton® X-100=nonionic detergent (see Merck Index 10th edition 1983 p. 971, Merck & Co, Rahway, U.S.A.)

Lipase was from Sigma Chemical Company, U.S.A.

dioactivity was measured in the remaining liquid; the results are set forth in Table 1 below.

In separation experiments goat antiapo(a) was replaced with sheep antiapo(a) and monoclonal antiapo(a). These antibodies were tested in soluble as well as in solid-phase-bound form. Decanting suspension was excluded when solid-phase-bound antiapo(a)s were used. The results obtained were in agreement with that presented in Table 1.

TABLE 1

|  | Acidic pH | | Pretreating method | Alkaline pH | | Untreated |
|---|---|---|---|---|---|---|
| Serum sample | 0.2 M HCl 41.0 U/l | 0.2 M citric acid 25.2 U/l | 0.2 M H$_3$PO$_4$ 28.4 U/l | 0.2 M Na$_3$PO$_4$ 354 U/l *CV = 4.2% | 0.13 M NaOH 333 U/l *CV = 7.0% | 7.7 U/l |
| Pretreating solution | 0.2M HCl | 0.2 M citric acid | 0.2 M H$_3$PO$_4$ | 0.2 M Na$_3$PO$_4$ | 0.13 M NaOH |  |
| Dilution ratio | 1:1 | 1:1 | 1:1 | 1:1 | 1:1 |  |
| Time | 20 h | 20 h | 20 h | 1 h | 2h |  |

*CV is the variance between assays comprising the dilutions for which a measured value U/l could be read off on a standard curve (1/162, 1/486, 1/1458)

In experiments 1 and 4 apo(a) has been determined in units (U) per liter relatively to a reference serum. This is of no relevance for the conclusions that may be drawn from the results.

EXAMPLE 1

Pretreatment of serum at acidic and alkaline pH 1.1 Pretreatment:

(a) Alkaline pH. Equal volumes of serum and 0.13 M NaOH were mixed and incubated at room temperature (=RT) for 2 hours, whereupon phosphate buffer I was added up to an 18-fold dilution of the sample. The pH measured initially was 12.0, whereupon it decreased to about 11.7 during incubation.

(b) Acidic pH. Equal volumes of serum and 0.2 M HCl were mixed and incubated at RT for 20 hours, whereupon phosphate buffer I was added up to an 18-fold dilution of the sample. The pH initially was about 1 and then rose slightly during incubation.

(c) Alkaline buffer system. Equal volumes of serum and 0.2 M trisodium phosphate were mixed and incubated at RT for 1 hour, whereupon phosphate buffer I was added up to an 18-fold dilution of the sample. The pH was found to be about 11.7 during the entire period of incubation.

1.2 Test method for determining how the pretreatment step affects availability of antigenic determinants.

50 μl from the reaction mixture of step 1 was diluted according to the dilution scheme 1/18–1/54–1/1-62–1/489–1/1458–1/4374. Each dilution was mixed with 50 μl of mouse antiapo(a) $^{125}$I and incubated for 1 hour at RT, whereupon 50 μl of goat antiapo(a) was added. The reaction mixture was kept standing for 0.5 hours at RT. This was followed by precipitation of the resultant complex with the aid of solid-phase-bound anti-antibodies (2 ml Decanting Suspension, 0.5 hr and RT). The suspension was centrifuged, the supernatant then being removed by decantation and discarded. Ra- The result are set forth as the U apo(a)/l concentration read off. They show clearly and unambiguously that the pretreatment is of decisive importance for allowing the immune reaction to proceed optimally.

They also show that a sodium hydroxide solution is far more effective than a hydrochloric acid solution. The serum samples studies have been diluted as indicated in the Table. The various dilutions have been treated as according to 1.1 and apo(a) has been quantified as according to 1.2.

By increasing the 0.13 m NaOH treatment time it could be shown that for a given dilution the uptake was lowered. This may be taken to indicate that antigenic determinants have been destroyed irreversibly.

EXAMPLE 2

Comparison of pretreatment according to the invention and prior art pretreatment 2.1 Pretreatment:

Equal volumes of serum and pretreating solution were mixed and incubated for 2–16 hours, whereupon the sample was diluted 20-fold with phosphate buffer I. The testing method according to 1.2 was then applied to the reaction solutions. Treating solutions, treating times and treating temperatures are set forth in Table 2. Results are set forth in Table 3.

TABLE 2

| Treating solution | Treating time | Treating temp |
|---|---|---|
| 0.5% SDS | 16 h | RT |
| 2.5% SDS | 16 h | RT |
| 4M Urea | 2 h | RT |
| 6M Urea | 2 h | RT |
| 2M Guanidine - HCl | 2 h | RT |
| 6M Guanidine - HCl | 2 h | RT |
| 2% Triton ® X - 100 | 16 h | RT |
| 10% Triton ® X - 100 | 16 h | RT |
| 1% Renex ® 30 | 16 h | RT |
| 5% Renex ® 30 | 16 h | RT |
| 500 U/ml Lipase | 16 h | 37° C. |
| 100 U/ml Lipase | 16 h | 37° C. |
| 0.13 M NaOH | 2 h | RT |

TABLE 3

| Sample | Dilution | SDS 0.5% | SDS 2.5% | UREA 4 M | UREA 6 M | GUANIDINE HCl 2 M | GUANIDINE HCl 6 M | TRITON X100 2% | TRITON X100 10% | RENEX 30 1% | RENEX 30 5% | LIPASE 500 U/l | LIPASE 100 U/l | Untreated |
|---|---|---|---|---|---|---|---|---|---|---|---|---|---|---|
| Lp(a) | 1/20 | 10.1 | 18.8 | 10.0 | 9.6 | 10.0 | 10.7 | 11.7 | 11.7 | 11.4 | 10.9 | 10.8 | 10.9 | 10.7 |
| | 1/60 | 5.3 | 13.3 | 5.4 | 5.3 | 5.6 | 6.3 | 5.9 | 6.0 | 5.8 | 5.6 | 5.6 | 5.8 | 5.5 |
| | 1/180 | 3.6 | 7.0 | 3.6 | 3.8 | 3.6 | 4.1 | 3.8 | 3.7 | 3.8 | 3.6 | 3.6 | 3.8 | 3.8 |
| | 1/540 | 3.0 | 4.5 | 3.2 | 3.1 | 3.1 | 3.3 | 3.2 | 3.2 | 3.0 | 3.8 | 3.2 | 3.1 | 3.2 |

The results are presented as % binding of total amount of tracer added (uptake). They show that delipidating methos employed earlier are ineffectual.

EXAMPLE 3

Comparative studies of a serum sample pretreated according to the invention, versus a reference sample containing affinity purified apo(a)

3.1 Affinity purification of apo(a) from serum treated according to 1.1 (a). Goat antiapo(a) antiserum was bound covalently to CNBr-activated Sepharose ® 4B (Pharmacia AB, Sweden) according to the method recommended by the producer (see also U.S. Pat. No. 3,645,852). 20 ml of the immunosorbent suspension obtained was mixed with 5 ml of NaOH-treated sample according to 1.1 (a) and diluted with phosphate buffer (pH 7.4, 0.05 M) to a total volume of about 65 ml. The resultant suspension was packed in a column and eluted in accordance with Table 4.

TABLE 4

| Step | Eluant | pH eluant | Peak No. | Volume |
|---|---|---|---|---|
| 1 | wash phosphate buffer | pH 7.4 | | 2 × gel |
| 2 | 0.1 M acetate buffer + 0.5 M NaCl | pH 4.5 | 1 | 2 × gel |
| 3 | phosphate buffer | pH 7.4 | 2 | 2 × gel |
| 4 | * 0.1 M glycine buffer + 0.5 M NaCl | pH 2.8 | 3 | 2 × gel |
| 5 | same as 3 | | 4 | 2 × gel |
| 6 | *same as 4 | | 5 | 2 × gel |
| 7 | same as 3 | | 6 | 2 × gel |
| 8 | *same as 4 | | 7 | 2 × gel |
| 9 | same as 3 | | 8 | 2 × gel |
| 10 | **guanidine - HCl 6 M in phosphate buffer | pH 6.0 | 9 | 2 × gel |
| 11 | same as 3 | | | 2 × gel |

*Eluates with glycine buffer were neutralized with phosphate buffer
**Fractions with guanidine - HCl were desalted on PD-10 columns packed with Sephadex ® G-25 (Pharmacia AB, Sweden), immediately after elution.

3.2 A dilution series of serum containing apo(a) treated according to 1.1 (a) and a dilution series of a known amount of affinity purified apo(a) were subjected to the measuring method according to 1.2. The apo(a) concentration was within the range of 0.06–20 U/l. The measurement values obtained were plotted against each concentration so that one dose-response curve could be established for affinity purified apo(a) and one for the serum sample. The two curves were perfectly parallel which shows that the pretreatment step of the invention is fully satisfactory from an immunological point of view.

EXAMPLE 4

Correlation between pretreated samples analyzed according to 1.2 and untreated samples analyzed according to the so-called "rocket" method "Rocket" analysis means electroimmunoassay (Laurell B, Anal. Biochem. 15/1966/p.45-). The method is one of those most commonly employed in apolipoprotein analyses.

15 serum samples were subjected to (i) a pretreatment according to 1.1 (a), followed by measuring according to 1.2, and (ii) electroimmunoassay according to Laurell B. The results can be inferred from Table 5.

TABLE 5

| Sample No. | Rocket mg/l | Method according to 1.2 U/l |
|---|---|---|
| 1 | 680 | 850 |
| 2 | 580 | 750 |
| 3 | 470 | 511 |
| 4 | 420 | 457 |
| 5 | 420 | 387 |
| 6 | 260 | 225 |
| 7 | 260 | 270 |
| 8 | 210 | 230 |
| 9 | 210 | 140 |
| 10 | 150 | 164 |
| 11 | 1 300 | 1 480 |
| 12 | 730 | 1 072 |
| 13 | —* | 13 |
| 14 | —* | 26 |
| 15 | —* | 4 |

*apo(a) could not be detected due to the low sensitivity of the "Rocket"-method.

It is evident from the results above that the two methods will produce inter-correlating values.

EXAMPLE 5

Pretreatment according to the invention of samples containing apo AI and apo B

Three different serum samples were subjected to the pretreatment of step 1.1. (c) (20-fold instead of 18-fold dilution), whereupon the testing procedure of step 1.2 with appropriate antibody reagents was applied. For antibody reagents see under heading "Reagents". The same samples without pretreatment but diluted 20-fold with phosphatebuffer I were also analyzed according to 1.2.

The results of the pretreatment were satisfactory for determining the apo proteins in question by an immunoassay.

The invention will be further defined in the attached claims forming part of this specification.

We claim:

1. A method for carrying out immunochemical assays for the lipoprotein, Lp(a), and/or the apolipoprotein, apo(a), which comprises
    (a) subjecting a sample suspected for containing Lp(a) and/or apo(a) to an environment where the pH is above about 9.0 or below about 3.0, for a time between 5 minutes and 20 hours, without causing denaturation of said Lp(a) or apo(a),
    (b) adjusting the pH of the mixture resulting from step (a) to a value suitable for an immune reaction between Lp(a) or apo(a) and anti-apo(a) antibodies,
    (c) reacting the mixture resulting from step (b) with anti-apo(a) antibodies.

(d) measuring the amount of immune complexes formed in step (c), and (e) relating the measurement of step (d) to the amount of Lp(a) and/or apo(a) in said sample.

2. A method according to claim 1 wherein the pH of the treatment step is adjusted to a value selected within the range of from 0 to 3 or within the range from 9.0 to 14.0.

3. A method according to claim 1 wherein the pH of the pretreatment step is adjusted to a value higher than 10.0.

4. A method according to claim 1 wherein in that the pH of the pretreatment step is adjusted to a value selected within the range of from 9 to 14.

* * * * *